United States Patent
Weiss

(10) Patent No.: US 10,292,773 B2
(45) Date of Patent: May 21, 2019

(54) POSITION DETERMINATION SYSTEM

(71) Applicant: KONINKLIJKE PHILIPS N.V., Eindhoven (NL)

(72) Inventor: Steffen Weiss, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 323 days.

(21) Appl. No.: 15/102,784

(22) PCT Filed: Dec. 8, 2014

(86) PCT No.: PCT/EP2014/076806
§ 371 (c)(1),
(2) Date: Jun. 8, 2016

(87) PCT Pub. No.: WO2015/086479
PCT Pub. Date: Jun. 18, 2015

(65) Prior Publication Data
US 2016/0310219 A1   Oct. 27, 2016

(30) Foreign Application Priority Data

Dec. 10, 2013   (EP) ..................................... 13196474

(51) Int. Cl.
*A61B 5/05* (2006.01)
*A61B 34/20* (2016.01)
(Continued)

(52) U.S. Cl.
CPC .............. *A61B 34/20* (2016.02); *A61B 5/055* (2013.01); *A61B 5/066* (2013.01); *A61B 6/488* (2013.01);
(Continued)

(58) Field of Classification Search
CPC ......... A61B 34/20; A61B 6/488; A61B 5/066; A61B 5/055; A61B 2560/0233;
(Continued)

(56) References Cited

U.S. PATENT DOCUMENTS 6,351,662 B1   2/2002   Franck
7,697,147 B2   4/2010   Kindlein
(Continued)

FOREIGN PATENT DOCUMENTS

EP   0673661 A2   9/1995
EP   2208460 A1   7/2010
(Continued)

OTHER PUBLICATIONS

Razminia, M. et al "Nonfluoroscopic Catheter Ablation of Cardiac Arrhythmias in Adults: Feasibiliy, Safety, and Efficacy", Journal of Cardiovascular Electrophysiology, vol. 23, No. 10, pp. 1078-1086, 2012.
(Continued)

*Primary Examiner* — Sanjay Cattungal

(57) ABSTRACT

At an imaging site an imaging device (14) generates an image of a subject (4) and an imaging light markers generation device (6) generates light markers at locations on a surface of the subject before an interventional procedure is performed. At an interventional site an interventional light markers generation device (17) generates light markers at the locations on the surface of the subject (4) and a localization device (25, 27) determines the position of a catheter during the interventional procedure. A position determination unit (29) then determines the position of the catheter within the pre-interventional image based on the position of the catheter determined by the localization device and provided spatial relations between the devices used for generating the image and the light markers and for localizing (Continued)

the catheter. This allows showing the position of the catheter within the pre-interventional image without necessarily using x-rays.

20 Claims, 8 Drawing Sheets

(51) Int. Cl.
*A61B 5/055* (2006.01)
*A61B 5/06* (2006.01)
*A61B 6/00* (2006.01)
*A61B 90/00* (2016.01)
*A61M 25/01* (2006.01)

(52) U.S. Cl.
CPC ............... *A61B 2034/2051* (2016.02); *A61B 2034/2061* (2016.02); *A61B 2090/364* (2016.02); *A61B 2090/3937* (2016.02); *A61B 2560/0233* (2013.01); *A61M 2025/0166* (2013.01)

(58) Field of Classification Search
CPC ...... A61B 2090/364; A61B 2090/3937; A61B 2034/2061; A61B 2034/2051; A61M 2025/0166
USPC .......................................... 600/424; 606/130
See application file for complete search history.

(56) References Cited

U.S. PATENT DOCUMENTS

| 2004/0034297 A1 | 2/2004 | Darrow | |
| 2004/0162486 A1 | 8/2004 | Stoianovici | |
| 2009/0251709 A1* | 10/2009 | Kindlein | A61B 6/08 356/608 |
| 2013/0033700 A1* | 2/2013 | Hallil | G01B 11/00 356/72 |

FOREIGN PATENT DOCUMENTS

| EP | 2594197 A1 | 5/2013 |
| JP | 2011172712 A | 9/2011 |
| WO | 2007113713 A2 | 10/2007 |
| WO | 2011113482 A1 | 9/2011 |
| WO | 2012127353 A1 | 9/2012 |
| WO | 2012149548 A2 | 11/2012 |
| WO | 2012177867 A2 | 12/2012 |

OTHER PUBLICATIONS

Lemery M.D, Robert, "Interventional Electrophysiology at the rossroads: Cardiac Mapping, Ablation and Pacing without Fluoroscopy", Journal of Cardiovascular Electrophysiology, vol. 23, No. 10, pp. 1087-1091, 2012.

* cited by examiner

POSITION DETERMINATION SYSTEM

CROSS-REFERENCE TO PRIOR APPLICATIONS

This application is the U.S. National Phase application under 35 U.S.C. § 371 of International Application No. PCT/EP2014/076806, filed on Dec. 8, 2014, which claims the benefit of European Patent Application No. 13196474.4, filed on Dec. 10, 2013. These applications are hereby incorporated by reference herein.

FIELD OF THE INVENTION

The invention relates to a position determination system, method and computer program for determining a position of a catheter, which is located within a subject, in an image of the subject during an interventional procedure. The invention relates further to a localization system for localizing the catheter within the subject during the interventional procedure and a calibration method for calibrating the position determination system.

BACKGROUND OF THE INVENTION

Conventional catheter ablation procedures in electrophysiology (EP) can be guided by x-ray fluoroscopy, often complemented by an electromagnetic tracking (EMT) system for tracking a catheter. For the guidance by x-ray fluoroscopy an x-ray fluoroscopy system is used, which acquires x-ray projection images during the catheter ablation procedure. The x-ray projection images can be registered with a pre-operative three-dimensional image like a computed tomography (CT) or magnetic resonance (MR) image, in order to provide three-dimensional anatomical information during the catheter ablation procedure. In particular, the position of the catheter tracked by the EMT system may be shown within the pre-operative three-dimensional image, in order to show the position of the catheter relative to an inner three-dimensional anatomy of a patient. However, acquiring the x-ray projection images leads to a relatively high radiation dose applied to the patient.

SUMMARY OF THE INVENTION

It is an object of the present invention to provide a position determination system, method and computer program for determining a position of a catheter, which is located within a subject, in an image of the subject during an interventional procedure, which allow for a reduction of the radiation dose applied to the subject, especially for a complete avoidance of x-rays. It is a further object of the present invention to provide a localization system for localizing the catheter within the subject during the interventional procedure and a calibration method for calibrating the position determination system.

In a first aspect of the present invention a position determination system for determining a position of a catheter, which is located within a subject, in an image of the subject during an interventional procedure is presented, wherein the position determination system comprises:
  an imaging device for generating an image of the subject, before the interventional procedure is performed, at an imaging site,
  an imaging light markers generation device for generating light markers at locations on a surface of the subject, before the interventional procedure is performed, at the imaging site,
  a localization device for determining the position of the catheter during the interventional procedure at an interventional site,
  an interventional light markers generation device for generating light markers at the locations on the surface of the subject at the interventional site,
  a spatial relations providing unit for providing an imaging spatial relation between the imaging device and the imaging light markers generation device and an interventional spatial relation between the localization device and the interventional light markers generation device, and
  a position determination unit for determining the position of the catheter within the generated image based on the position of the catheter determined by the localization device and the imaging and interventional spatial relations.

Due to the imaging spatial relation between the imaging device and the imaging light markers generation device, the interventional spatial relation between the localization device and the interventional light markers generation device and the generation of the light markers by the imaging light markers generation device and the interventional light markers generation device at the same locations on the surface of the subject, the position of the catheter within the generated image can be accurately determined, without necessarily applying x-rays to the subject.

The imaging site is the site at which the imaging by the imaging device and the generation of the light markers by the imaging light markers generation device take place. For instance, the imaging site may be an imaging room in which the imaging device and the imaging light markers generation device are located. The interventional site is the site at which the interventional procedure is performed. For example, it may be an operation room comprising the localization device and the interventional light markers generation device.

The imaging device is preferentially adapted to generate a three-dimensional image of the subject like a computed tomography image and/or a magnetic resonance image. The localization device is preferentially adapted to determine the position of the catheter by using an EMT and/or an optical shape sensing tracking (OSST) technique. The imaging light markers generation device and the interventional light markers generation device preferentially comprise several light sources, especially lasers, for generating the light markers at the locations on the surface. Preferentially, the imaging light markers generation device and the interventional light markers generation device are adapted to generate three or more light markers at three or more locations on the surface. If lasers are used, the light markers can be generated very accurately due to the coherence properties of the laser light, thereby further increasing the accuracy of determining the position of the catheter within the generated image.

The imaging light markers generation device preferentially comprises light sources emitting rays in accordance with a first ray geometry for generating the light markers and the interventional light markers generation device preferentially comprises light sources emitting rays in accordance with a second ray geometry for generating the light markers, wherein the first ray geometry and the second ray geometry are preferentially the same. The spatial relations providing unit is preferentially a storing unit in which the spatial relations are stored already and from which the spatial relations can be retrieved for providing the same. The stored spatial relations can be determined in advance during a calibration procedure.

The imaging light markers generation device and the imaging device may be separate devices or they may form an integrated device, wherein in the latter case the imaging light markers generation device may comprise light sources attached to the imaging device. Also the interventional light markers generation device and the localization device may be separate devices or they may form an integrated device, wherein in the latter case the interventional light markers generation device may comprise light sources attached to the localization device. Integrating the imaging light markers generation device and the imaging device and/or the interventional light markers generation device and the localization device can lead to reduced space requirements.

It is preferred that the imaging light markers generation device and/or the interventional light markers generation device comprise a bridge structure for bridging the subject, wherein light sources for generating the light markers are attached to the bridge structure. The bridge structure preferentially comprises a part being above a subject support of the position determination system, wherein the light sources may be attached to this part, in order to illuminate the surface of the subject from above, when the subject is arranged on the subject support.

In an embodiment the imaging light markers generation device and/or the interventional light markers generation device are adapted such that the different generated light markers have different visual appearances. For instance, different generated light markers can have different colors and/or different shapes. Moreover, the imaging light markers generation device and/or the interventional light markers generation device can be adapted such that the different generated light markers are accompanied by labels labeling the respective light markers. The different visual appearances and/or labels can be used to guide a user in using corresponding rays of the respective light markers generation device for generating corresponding light markers at the locations on the surface.

The imaging light markers generation device and/or the interventional light markers generation device are preferentially adapted such that the different generated light markers are light points and for instance not light lines.

The position determination system preferentially further comprises a subject support for supporting the subject, wherein the subject support is adapted to position the subject with six degrees of freedom. Since the subject support is adapted to position the subject with six degrees of freedom, the position determination system can be used in a configuration, in which the ray geometries used by the imaging light markers generation device and the interventional light markers generation device are the same, i.e. in this situation the light markers generated by the interventional light markers generation device can still be generated at the locations on the surface of the subject, at which also the light markers have been generated by the imaging light markers generation device, by positioning the six degrees of freedom subject support and thus the subject accordingly.

The position determination system may further comprise a calibration phantom comprising first markers for marking locations at which the light markers generated by the interventional light markers generation device are to be located during a calibration procedure and second markers for marking locations at which the catheter is to be located during the calibration procedure while the localization device determines the position of the catheter, wherein the spatial relations providing unit is adapted to determine the interventional spatial relation based on the positions of the catheter, which have been determined by the localization device while the catheter was located at the second markers and the light markers were located at the first markers. This allows the spatial relations providing unit to accurately determine the interventional spatial relation, which may be stored in the spatial relations providing unit and which may be retrieved during the interventional procedure for determining the position of the catheter within the generated image.

In another aspect an imaging system for imaging a subject and for being used together with the localization system for forming the position determination system is presented, wherein the imaging system comprises:
  an imaging device for generating an image of the subject, before the interventional procedure is performed, at an imaging site,
  an imaging light markers generation device for generating light markers at locations on a surface of the subject, before the interventional procedure is performed, at the imaging site.

In a further aspect of the present invention a localization system for localizing a catheter within a subject during an interventional procedure and for being used together with the imaging system and for forming the position determination system is presented, wherein the localization system comprises:
  a localization device for determining the position of a catheter during the interventional procedure at an interventional site,
  an interventional light markers generation device for generating light markers at locations on the surface of the subject, at which the imaging light markers generation device of the imaging system has also generated light markers, at the interventional site,
  a spatial relations providing unit for providing an imaging spatial relation between the imaging device of the imaging system and the imaging light markers generation device and an interventional spatial relation between the localization device and the interventional light markers generation device, and
  a position determination unit for determining the position of the catheter within the generated image based on the position of the catheter determined by the localization device and the imaging and interventional spatial relations.

In another aspect a light markers generation device for being used by the position determination system is presented, wherein the light markers generation device comprises a bridge structure for bridging a subject and light sources attached to the bridge structure and wherein the light sources are adapted to generate light markers on a surface of a subject. The light markers generation device may be a separate device, i.e. not integrated with, for instance, an imaging device or a localization device, such that a single light markers generation device may be used together with several other devices, for instance, a single light markers generation device may be used for different imaging devices and/or for different localization devices.

In a further aspect of the present invention a position determination method for determining a position of a catheter, which is located within a subject, in an image of the subject during an interventional procedure and for being used by the position determination system is presented, wherein the method comprises:
  generating an image of the subject, before the interventional procedure is performed, at an imaging site by an imaging device, generating light markers at locations on a surface of the subject, before the interventional procedure is performed, by an imaging light markers generation device at the imaging site, generating light markers at the locations on the surface of the subject by an interventional light markers generation device at an interventional site, providing an imaging spatial relation between the imaging device and the imaging light markers generation device and an interventional spatial relation between the localization device and the interventional light markers generation device by a spatial relations providing unit, determining the position of the catheter within the subject during the interventional procedure by a localization device at the interventional site, and determining the position of the catheter within the generated image based on the position of the catheter determined by the localization device and the imaging and interventional spatial relations by a position determination unit.

In an embodiment the method further includes permanently marking the locations on the surface of the subject at the imaging site, wherein the generation of the light markers at the interventional site includes generating the light markers at the marked locations on the surface. Here the term "permanently" means that the locations are marked such that they are still indicated, even if the light markers are not present anymore. For instance, a pen can be used for permanently marking the locations, wherein of course the permanent markers can be removed again, if desired. This allows ensuring that the light markers generated by the imaging light markers generation device and the light markers generated by the interventional light markers generation device are really generated at the same locations on the surface of the subject in a relatively simple way.

In another aspect of the present invention a calibration method for calibrating the localization system is presented, wherein the calibration method comprises:

providing a calibration phantom comprising first and second markers, generating light markers by the interventional light markers generation device at the first markers of the calibration phantom, locating the catheter at the second locations and determining the positions of the catheter by the localization device, when the catheter is located at the second locations, for generation calibration positions, determining an interventional spatial relation between the localization device and the interventional light markers generation device based on the calibration positions.

In a further aspect of the present invention a localization computer program for localizing a catheter within a subject during an interventional procedure is presented, wherein the localization computer program comprises program code means for causing:

a localization device of the localization system to determine a position of the catheter during the interventional procedure, a spatial relations providing unit of the localization system to provide an imaging spatial relation between the imaging device and the imaging light markers generation device of the imaging system and an interventional spatial relation between the localization device and the interventional light markers generation device of the localization system, and a position determination unit of the localization system to determine the position of the catheter within an image generated by the imaging device based on the position of the catheter determined by the localization device and the imaging and interventional spatial relations, when the computer program is run on a computer controlling the localization device, the spatial relations providing unit and the position determination unit.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
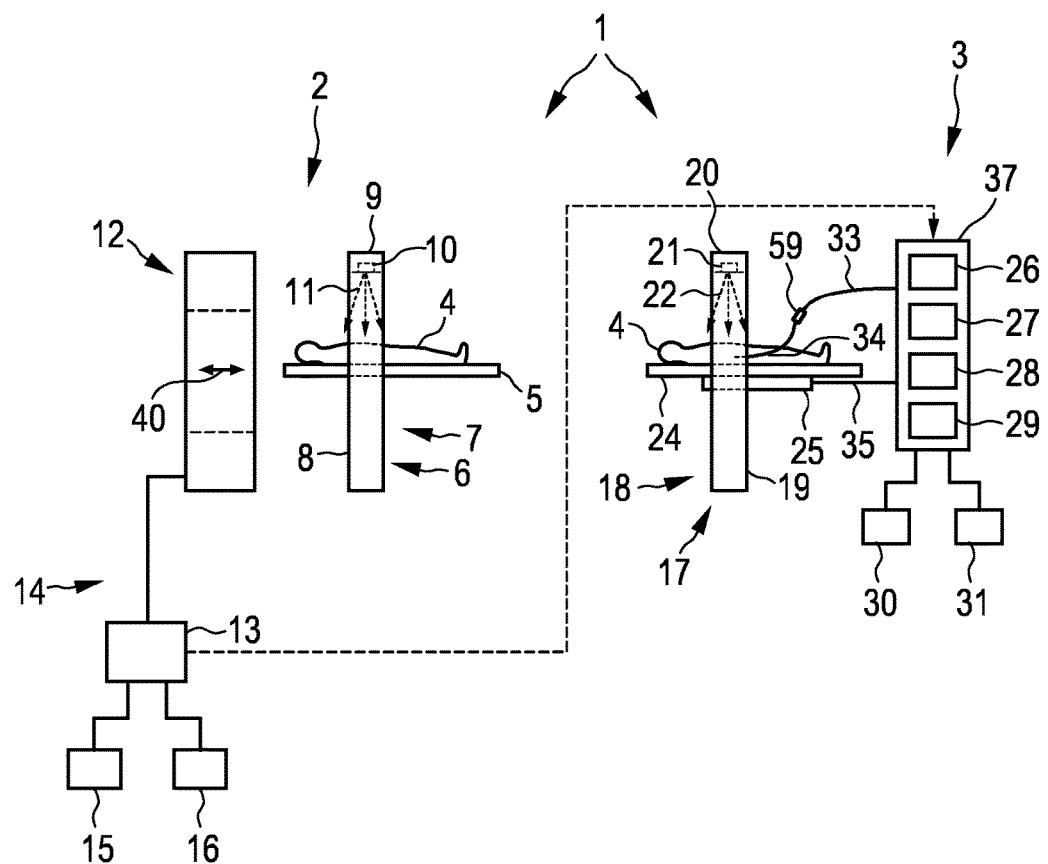
FIG. 1 shows schematically and exemplarily an embodiment of a position determination system for determining a position of a catheter, which is located within a subject, in an image of the subject during an interventional procedure.

FIG. 1 shows schematically and exemplarily an embodiment of a position determination system for determining a position of a catheter, which is located within a subject, in an image of the subject during an interventional procedure. The position determination system 1 comprises an imaging device 14 for generating an image of the subject 4 at an imaging site, for instance, within an imaging room before the interventional procedure is performed. In this embodiment the imaging device 14 is an MR imaging device comprising an MR data acquisition unit 12, an MR control unit 13, an input unit 15 like a keyboard, a computer mouse, a touch pad, et cetera, and a display 16. The MR data acquisition unit 12 is adapted to acquire MR data of the subject 4 lying on a subject support 5 like a support table, when the subject support 5 with the subject 4 has been moved into the MR data acquisition unit 12. Thus, the subject support 5 is movable into the MR data acquisition unit 12 for acquiring MR data and out of the MR data acquisition unit 12, after the MR data have been acquired, in the directions indicated in FIG. 1 by the double arrow 40. The MR control unit 13 is adapted to control the MR data acquisition unit 12 and optionally also the subject support 5 and to reconstruct an MR image based on the acquired MR data. The reconstructed MR image can be shown on the display 16. The input unit 15 can be used to, for instance, initiate a desired MR data acquisition and/or MR reconstruction procedure.

The position determination system 1 further comprises an imaging light markers generation device 6 for generating light markers at locations on a surface of the subject at the imaging site. In this embodiment the imaging light markers generation device 6 is adapted to generate light points as light markers such that it can also be regarded as being an imaging light points generation device.

Figure 2:
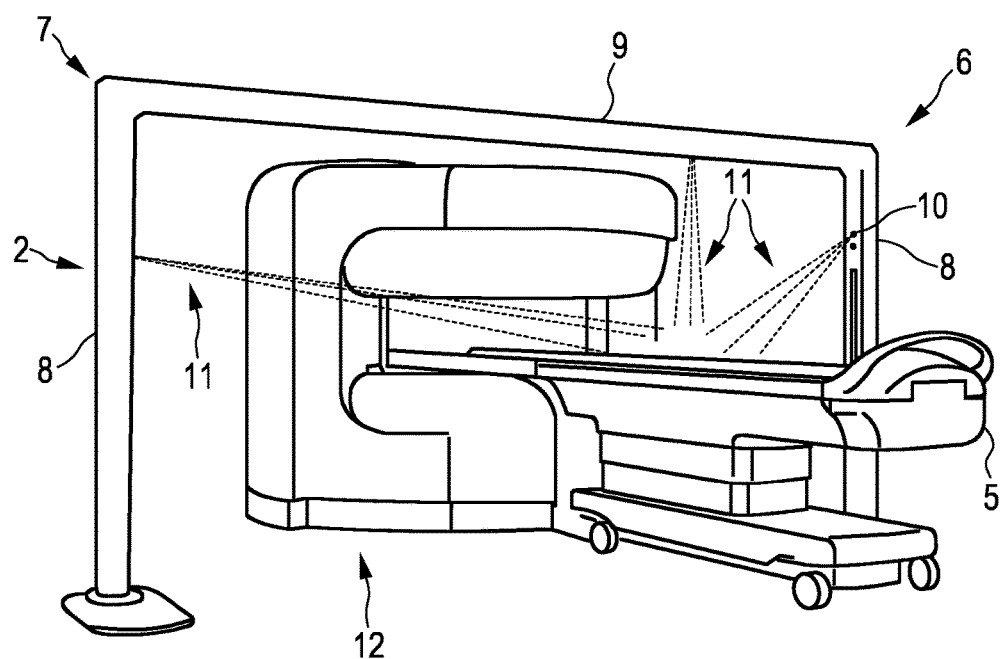
FIG. 2 shows schematically and exemplarily an embodiment of an imaging system of the position determination system.

The imaging light points generation device 6 comprises a bridge structure 7 having vertical parts 8 carrying a horizontal part 9 and lasers 10. A perspective view of an embodiment of the MR data acquisition unit 12, the imaging light points generation device 6 and the subject support 5 is schematically and exemplarily illustrated in FIG. 2. As can be seen in this figure, the vertical parts 8 of the bridge structure 7 are located at opposite sides of the subject support 5 and the horizontal part 9 is carried by the vertical parts 8 and extends above the subject support 5 and thus above the subject, when the subject is arranged on the subject support 5, i.e. the bridge structure 6 bridges the subject when lying on the subject support 5. In the example shown in FIG. 2 lasers 10 are arranged at the vertical parts 8 and the horizontal part 9 in order to generate the light points on the surface of the subject from different directions by using the rays 11.

Before imaging, the subject 4 may be located in front of the MR data acquisition unit 12 in an imaging position, i.e. in a position relative to the subject support 5 that will be used during imaging, and within the bridge structure 7 as illustrated in FIG. 1 such that light points can be generated on the surface of the subject 4. The locations of the light points on the surface of the subject 4 can be marked by using, for instance, a permanent color pen. Then, the subject support 5 and thus the subject 4 are moved into the MR data acquisition unit 12, while the subject 4 is still in the imaging position, i.e. it is assumed that the subject 4 has not been moved relative to the subject support 5. The MR data are acquired by the MR data acquisition unit 12 and the MR control unit 13 reconstructs an MR image based on the acquired MR data. After the MR data have been acquired, the subject support 5 with the subject 4 is moved out of the MR data acquisition unit 12. The MR imaging device 14 and the imaging light points generation device 6 can be regarded as being parts of an MR imaging system 2 for generating an MR image.

The position determination system 1 further comprises a localization device for determining the position of the catheter 34 during the interventional procedure at an interventional site like an operation room at which the interventional procedure is performed. In this embodiment the catheter 34 has a hand grip 59. The catheter 34 is connected with a control unit 37 comprising a radiofrequency (RF) energy source 26 via a cable 33. While performing the interventional procedure, the catheter 34 is used within the subject 4 lying on a subject support 24. The tip of the catheter 34 comprises one or several electrodes for applying the RF energy within the subject 4, in order to perform, for instance, an ablation procedure. The tip of the catheter 34 further comprises an EM position sensor which interacts with an EM field generated by an EM field generator 25 arranged below the subject support 24. The EM field generator 25 is connected to the control unit 37 via a cable 35. The control unit 37 comprises a localization control unit 27 for controlling the EM field generator 25 and the EM position sensor arranged at the tip of the catheter 34 and for determining the position of the tip of the catheter 34 within the subject 4 based on EM signals generated by the EM field generator 25 and the EM position sensor at the tip of the catheter 34. The localization control unit 27 together with the EM field generator 25 and the EM position sensor at the tip of the catheter 34 form therefore the localization device for determining the position of the catheter during the interventional procedure at the interventional site.

Figure 3:
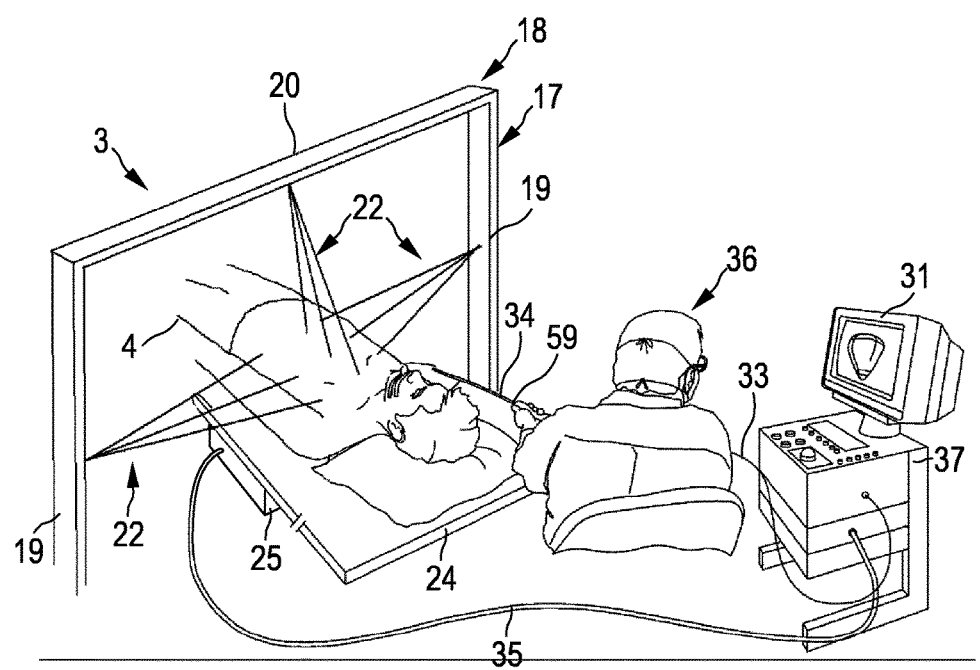
FIG. 3 shows schematically and exemplarily an embodiment of a localization system of the position determination system.

The position determination system 1 further comprises an interventional light points generation device 17 for generating light points at the locations on the surface of the subject 4, at which also the imaging light points generation device 6 has generated the light points, at the interventional site. Also the interventional light points generation device 17 comprises a bridge structure 18 with vertical parts 19 located at opposing sides of the subject support 24 and with an upper intermediate horizontal part 20 as schematically and exemplarily illustrated in FIG. 3. Lasers 21 are arranged at the horizontal part 20 and the vertical parts 19 for generating laser rays 22 which in turn generate the light points at the locations on the surface of the subject 4. In this embodiment the geometry of the rays 22 of the interventional light points generation device 17 and the geometry of the rays 11 of the imaging light points generation device 6 are the same. In order to position the subject 4 such that the light points generated by the interventional light points generation device 17 are arranged at the same locations at which also the light points have been generated by the imaging light points generation device 6, without modifying the geometry of the rays 22 of the interventional light points generation device 17, the subject support 24 has six degrees of freedom. Thus, if the locations used by the imaging light points generation device have been marked on the surface of the subject 4, the subject support 24 can be positioned such that also the light points generated by the interventional light points generation device 17 are arranged at the marked locations on the surface of the subject 4.

Figure 4:
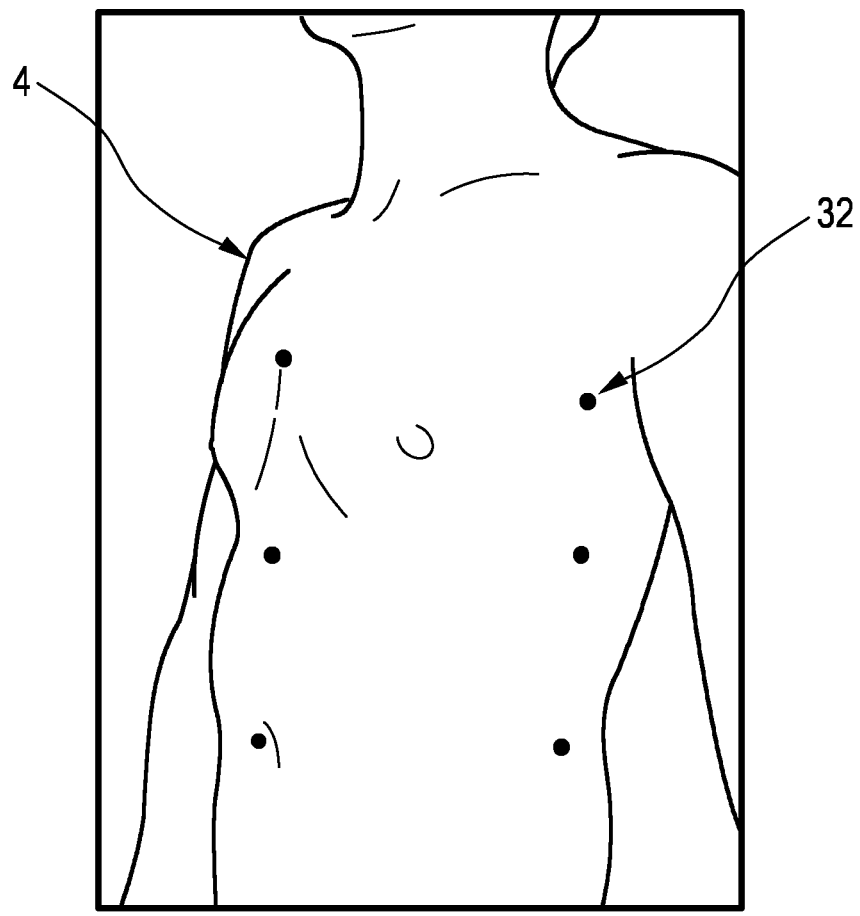
FIG. 4 illustrates exemplarily a distribution of light markers on a chest of a person.

FIG. 4 shows schematically and exemplarily preferred locations 32 on the subject 4, at which the light points should be generated. The light points 32 are preferentially distributed on the chest such that they do not cover the arms of the subject 4, because the arms are more likely to be moved by the subject 4.

The position determination system 1 further comprises a spatial relations providing unit 28 for providing an imaging spatial relation between the MR imaging device 14 and the imaging light points generation device 6 and an interventional spatial relation between the localization device 25, 27 and the interventional light points generation device 17. The position determination system 1 also comprises a position determination unit 29 for determining the position of the catheter 34 within the generated MR image based on the position of the catheter 34 determined by the localization device 25, 27 and the imaging and interventional spatial relations.

In particular, since the imaging light markers generation device 6 generates light markers at locations on a surface of the subject, the spatial relation between a subject coordinate system defined by the locations on the surface of the subject and a coordinate system of the imaging light markers generation device 6 is known from the geometry of rays used for generating the light markers. Moreover, since the spatial relations providing unit 28 provides the imaging spatial relation between the imaging device 14 and the imaging light markers generation device 6, i.e. since additionally the spatial relation between an imaging coordinate system of the imaging device 14 and the coordinate system of the imaging light markers generation device 6 is known, also the spatial relation between the subject coordinate system and the imaging coordinate system is known. Furthermore, since the interventional light markers generation device 17 generates the light markers at locations on the surface of the subject, which are equal to the locations on the surface of the subject, on which the light markers have been generated by the imaging light markers generation device 6, the geometry of the rays used by the interventional light markers generation device 17 for generating the light markers leads to the spatial relation between the subject coordinate system and a coordinate system of the interventional light markers generation device 17. Moreover, since in addition the spatial relations providing unit 28 provides the interventional spatial relation between the localization device 25, 27 and the interventional light markers generation device 17, i.e. between a localization coordinate system of the localization device 25, 27 and the coordinate system of the interventional light markers generation device 17, also the spatial relation between the subject coordinate system and the localization coordinate system is known. Thus, since the spatial relation between the imaging coordinate system and the subject coordinate system and the spatial relation between the localization coordinate system and the subject coordinate system are known, the position of the catheter 34 determined by the localization device 25, 27 can accurately be determined within the generated image. This determination of the position of the catheter 34 within the generated image does not necessarily require x-ray projection images, thereby allowing for a reduction of the radiation dose applied to the subject. In particular, it can lead to an interventional procedure which does not need any x-rays to be applied to the subject.

The imaging and interventional spatial relations may have been determined in advance in corresponding calibration steps, wherein the determined imaging and interventional spatial relations are stored in the spatial relations providing unit 28, in order to allow the spatial relations providing unit 28 to provide the imaging and interventional spatial relations during the interventional procedure.

The localization device, the spatial relations providing unit and the position determination unit together with the interventional light points generation device can be regarded as being components of a localization system 3 for localizing a catheter within a subject during an interventional procedure. In this embodiment the localization system 3 is integrated with the system for performing the interventional procedure, i.e. with the catheter and the RF energy source. The localization system 3 with the equipment for performing the interventional procedure may be located in a first room like an operation room, especially an EP lab, and the imaging system with the MR imaging device and the imaging light points generation device may be arranged an another room like an imaging room. Thus, although the generation of the MR image and the interventional procedure may take place in different rooms, the position of the catheter within the subject can still accurately be shown in the MR image during the interventional procedure. This allows a physician 36 to accurately navigate the catheter 34 within the subject 4 based on the inner anatomical structure of the subject 4 shown in the generated image.

Figure 5:
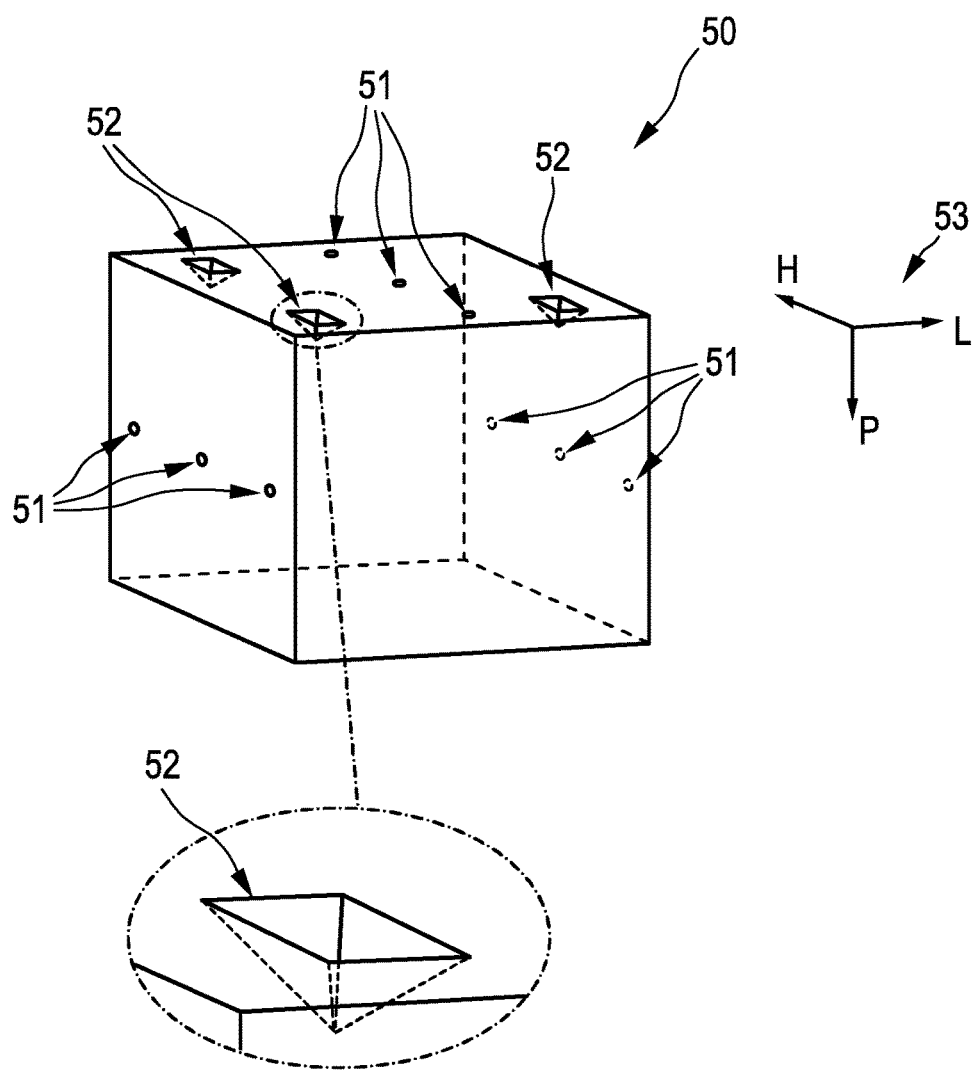
FIG. 5 shows schematically and exemplarily a calibration phantom.

For calibrating the interventional spatial relation a calibration phantom may be used. The calibration phantom may have the shape of a cube as schematically and exemplarily shown in FIG. 5. The calibration phantom 50 preferentially comprises first markers 51 for marking locations at which the light points generated by the interventional light points generation device 17 are to be located during the calibration procedure and at least three second markers 52 for marking locations at which the tip of the catheter 34 is to be located during the calibration procedure while the localization device determines the position of the tip of the catheter 34. A higher number of second markers adds to the overall precision of the calibration, which can be performed as a least square fit as known in the art. The first markers 51 are preferentially covered with a material that scatters light strongly and stronger than the rest of the surface of the calibration phantom 50. This may simplify the process of orienting the phantom to align with the light. The second markers 52 are preferentially made as dips in the calibration phantom 50 which are used to receive the catheter tip. One of the dips is shown in FIG. 5 in an enlarged view. The dips ensure that the tip is immobilized at an exactly defined position. Since most electrophysiology catheters have a spherical tip shape, the dips may for that purpose preferentially have a pyramidal shape such that a known position is achieved irrespective of the catheter diameter. Special phantoms with fitting dips may be used for other tip shapes. The spatial relations providing unit 28 may be adapted to determine the interventional spatial relation based on the positions of the tip of the catheter 34, which have been determined by the localization device, while the tip of the catheter 34 was located at the second markers 52 and the light points were located at the first markers 51, and based on known spatial relations between the first and second markers 51, 52. In FIG. 5 the coordinate system 53 is an LPH (Left, Posterior, Head) coordinate system, wherein during the calibration procedure the calibration phantom 50 may be oriented relative to the coordinate system 53 as indicated in FIG. 5. However, during calibration the calibration phantom 50 may also be oriented in another way.

Figure 6:
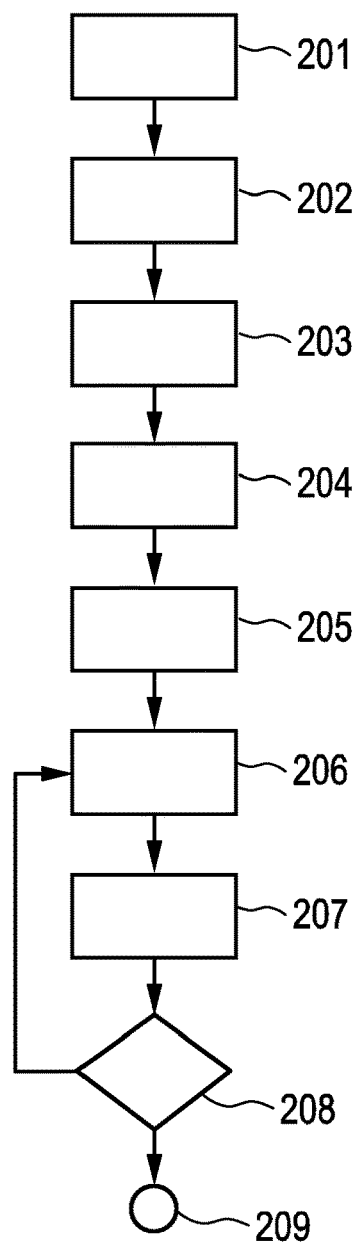
FIG. 6 shows a flowchart exemplarily illustrating an embodiment of a position determination method for determining a position of a catheter, which is located within a subject, in an image of the subject during an interventional procedure.

In the following an embodiment of a position determination method for determining a position of a catheter, which is located within a subject, in an image of the subject during an interventional procedure will be exemplarily described with reference to a flowchart shown in FIG. 6.

In step 201 light points 32 are generated at locations on the surface of the subject 4 at the imaging site like an imaging room by the imaging light points generation device 6. In step 202 the locations on the surface of the subject 4, at which the light points 32 are generated at the imaging site, are marked by using, for instance, a permanent color pen. In step 203 an MR image of the subject 4 is generated by using the MR imaging device 14 at the imaging site. Steps 201 to 203 may also be performed in another order. For instance, step 203 may be performed before steps 201 and 202. After the MR image has been generated, the subject 4 may be moved to an interventional site like an EP room or EP lab in which the interventional procedure may be performed.

In step 204 the subject 4 is arranged on the subject support 24 in an interventional position, i.e. in the position which should be used during the interventional procedure, wherein this interventional position is such that the interventional light points generation device 17 can generate light points 32 at the marked locations on the surface of the subject 4. In particular, the subject support 24 is moved such that the light points generated by the lasers of the interventional light points generation device 17 coincide with the locations marked in step 202. In step 205 an imaging spatial relation between the MR imaging device 14 and the imaging light points generation device 6 and an interventional spatial relation between the localization device 25, 27 and the interventional light points generation device 17 are provided by the spatial relations providing unit 28. In step 206 the position of the catheter 34 within the subject 4 during the interventional procedure while the subject 4 is in the interventional position is determined by the localization device 25, 27, and in step 207 the position of the catheter 34 within the generated MR image is determined based on the position of the catheter 34 determined by the localization device 25, 27 and the imaging and interventional spatial relations by the position determination unit 29 and the determined position is shown within the MR image on a display 31. In step 208 it is checked whether an abort criterion is fulfilled. The abort criterion may be that the interventional procedure has been completed or that the physician has input via an input unit 30 that the determination of the position of the catheter 34 within the generated MR image should be stopped. If the abort criterion is not fulfilled, the method continues with step 206. Otherwise the method ends in step 209. The position of the catheter, in particular, of the tip of the catheter, may therefore be continuously determined and shown within the MR image, while the catheter is moved within the subject, until the abort criterion is fulfilled.

Figure 7:
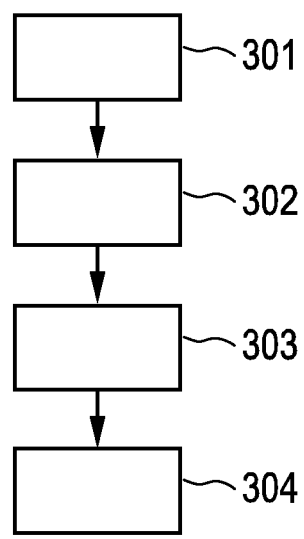
FIG. 7 shows a flowchart exemplarily illustrating a calibration method for calibrating the position determination system.

In the following an embodiment of a calibration method for calibrating the position determination system will exemplarily be described with reference to a flowchart shown in FIG. 7.

In step 301 the calibration phantom comprising the first and second markers is provided. For instance, the calibration phantom may be arranged on the subject support 24. In step 302 light points are generated by the interventional light points generation device 17 at the first markers of the calibration phantom and in step 303 the tip of the catheter 34 is located at the second locations and the positions of the tip of the catheter 34 are determined by the localization device 25, 27, when the tip of the catheter 34 is located at the second locations, thereby generating calibration positions. In step 304 the interventional spatial relation between the localization device 25, 27 and the interventional light points generation device 17 is determined based on the calibration positions and known spatial relations between the first and second markers. The interventional spatial relation can be stored in the spatial relations providing unit 28, in order to allow the spatial relations providing unit 28 to provide the interventional spatial relation during the interventional procedure.

In this embodiment the ray geometry provided by the interventional light points generation device 17 is fixed. Thus, in step 302 the light points are generated at the first markers of the calibration phantom by placing the calibration phantom accordingly, i.e. the calibration phantom is positioned such that the first markers coincide with the light points generated by the interventional light points generation device.

Conventional catheter ablation procedures are normally guided by x-ray fluoroscopy, often complemented by an EMT system. Some work steps are often also complemented by intracardiac echo (ICE) and transesophageal echo (TEE) imaging. Additionally, intracardiac electrograms (IE) can be acquired and provide position information based on a known cardiac excitation pattern.

In the article "Nonfluoroscopic Catheter Ablation of Cardiac Arrhythmias in Adults: Feasibility, Safety, and Efficacy" by M. Razmina et al., Journal of *Cardiovascular Electrophysiology*, 23(10):1078-1086 (2012) a catheter ablation procedure is described, which uses only IE, EMT and ICE for catheter guidance and no x-ray fluoroscopy. In this non-fluoroscopic (NF) procedure the catheter needs to be roved within the vascular system and cardiac chambers to "create" a roadmap for guidance during the procedure. In sync with this, manual segmentations need to be done by an additional operator during the intervention. However, there is no means to "look ahead", i.e. there is no anatomy information from locations where the catheter will go next but has not been yet. For example, there is no information available of pulmonary vein variants in atrial fibrillation (AF) patients that influence the ablation strategy. The position determination system described above with reference to FIGS. 1 to 4 therefore provides a pre-operative imaging for improving the guidance during the interventional procedure, in particular, for providing a three-dimensional roadmap for catheter guidance.

The position determination system preferentially comprises a pre-operative three-dimensional imaging modality like the above mentioned MR imaging modality or another three-dimensional imaging modality like a CT, rotational x-ray, positron emission tomography (PET) et cetera modality, which is equipped with a laser bridge, i.e. an imaging light points generation device, to mark specific points on the patient during pre-operative imaging. It preferentially further comprises an NF EP lab equipped with an EMT system, i.e. a localization device, and a second identical laser bridge, i.e. an interventional light points generation device, to allow patient positioning relative to that laser bridge. Moreover, a method to register the pre-operative dataset to the EMT system and to display at least parts of this dataset together with the catheter position derived from EMT is preferentially provided.

The pre-operative imaging modality may be equipped with a laser bridge as described above with reference to FIG. 2. The laser bridge does not produce lines, but the laser bridge may mark N points on the chest of the patient by using N distinct laser pointers in a fixed geometrical arrangement. The points are preferentially distributed on the chest such that they do not cover the arms of the patient. This is especially preferred, if the interventional procedure should be applied to the heart, because the arms are not in a fixed geometric relation to the heart of the patient. The laser colors may differ, or labels may be displayed besides the points to distinguish them. Not all rays/points provided by the system may be used for a specific patient. The EMT system may be equipped with a laser bridge system that has exactly the same ray geometry as the one used pre-operatively. The field generators of the EMT system are preferentially in a fixed known geometric relation to the laser bridge. Conveniently, the table with the patient can be moved in six degrees of freedom with respect to the laser bridge.

The field generator of the EMT system defines a coordinate system in which the catheter is tracked. Hence, it is preferentially in a fixed position relative to the laser bridge, which defines the pre-operative coordinate system. The field generator of the EMT system is preferentially positioned relative to the laser bridge only once during system set up, but may be rechecked for safety reasons. The calibration may be done using a special phantom, i.e. the above mentioned calibration phantom. The phantom has markers, i.e. first markers, that need to be aligned with the laser bridge. The phantom also has marked locations, i.e. second markers, with coordinates which are known relative to the coordinates of the first markers and thus relative to the laser bridge system, if the laser bridge is aligned with the first markers. During the calibration process these marked locations are approached by the catheter. At those locations the field generator senses the catheter positions in its own coordinate system. These matching points may be used to calculate the coordinate transform from the laser bridge system to the EMT system, i.e. the spatial relation between the interventional light points generation device and the localization device, which may be stored in the spatial relations providing unit.

In an embodiment during the pre-operative imaging procedure the patient is prepared in front of the MR bore or a bore of another imaging modality like a CT bore for pre-operative scanning A MR or CT light visor may be used to position the patient correctly for scanning in the isocenter of the system. Laser points from the bridge are then projected onto the patient, wherein these points are marked and labeled on the patient skin with permanent color pens. Only those points are used that do not project onto the arms. The patient is advanced into the bore and the first pre-operative scan is performed. The patient is then removed back to the front of the bore to confirm positioning. If the patient has moved, he/she may be repositioned to match laser points with skin marks and the scan be repeated. This scheme can avoid that more than one scan has to be redone. The pre-operative image data are transferred to the EMT system, for instance, via a DICOM (Digital Imaging and Communications in Medicine) import, wherein segmentations of an endovascular surface or further information may be derived from those data. The patient is then positioned under the laser bridge in the EP lab, wherein the table with six degrees of freedom is used to position the patient such that the laser points match the markers on the patient skin. The patient position may be rechecked repeatedly during the procedure. During the interventional procedure, which in this embodiment is a catheter procedure, catheters are tracked with the EMT system, i.e. with the localization device. Anatomic representations derived from the pre-operative data may be rendered together with models of the catheter to improve guidance.

The above described systems and methods are preferentially used to provide an endovascular surface together with an EMT catheter location to improve guidance of the catheter. However, further information may be extracted from the pre-operative image and shown to the user together with the EMT catheter location like wall thickness maps that may be pre-operatively calculated from the pre-operative image. Moreover, in myocardial biopsies biopsy target locations may be imaged pre-operatively with MR with good contrast, segmented, numbered, and provided as a work schedule during the interventional procedure. Critical structures that should be avoided with the catheter may be marked in advance and shown during the interventional procedure. The position determination system and method may be used in cardiac interventions, but also in non-cardiac interventions like in interventional procedures for treating major vessels in the neurovascular space.

Figure 8:
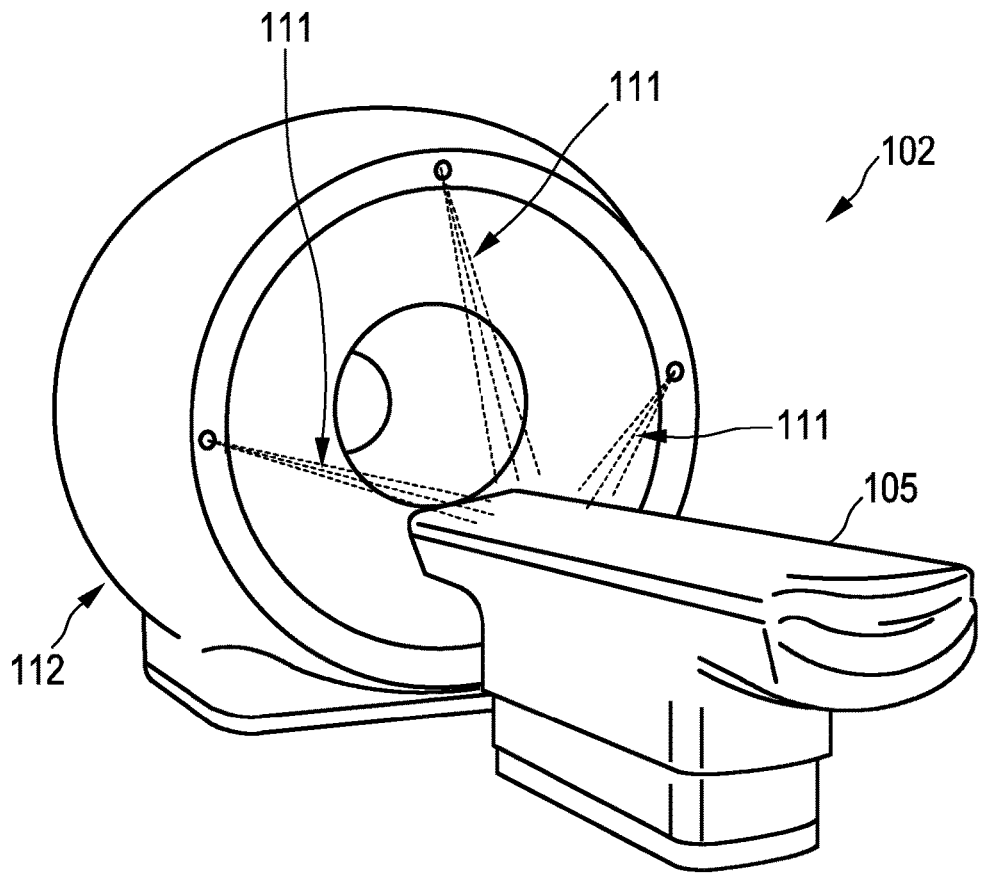
FIG. 8 shows schematically and exemplarily a further embodiment of an imaging system.

Although in the embodiments described above with reference to FIGS. 1 to 3 the imaging light points generation device and the interventional light points generation device have certain structures, in other embodiments they can be constructed in another way. For instance, they can comprise differently constructed bridge structures or they may not comprise any bridge structure. For instance, light sources may be integrated in the imaging device and/or in the localization system, in order to provide the imaging light points generation device and/or the interventional light points generation device, respectively. In particular, as schematically and exemplarily illustrated in FIG. 8, an imaging system 102 can comprise an MR data acquisition unit 112 with a subject support 105 and lasers integrated in the MR data acquisition unit 112 such that laser rays 111 emanate from the MR data acquisition unit 112. In a further embodiment the imaging device may be equipped with light sources for generating the light points on the surface of the subject and in addition a bridge structure with further light sources may be used for generating light points on the surface of the subject.

Although in above described embodiments the imaging light markers generation device and the interventional light markers generation device use the same fixed ray geometry for generating the light markers at the same locations on the surface of the subject, in another embodiment the imaging light markers generation device and/or the interventional light markers generation device may use different ray geometries, which may be fixed or modifiable. For instance, the imaging light markers generation device and/or the interventional light markers generation device may be adapted to modify the ray geometries such that the light markers are generated on the same locations at the imaging site and at the interventional site. The position determination unit may be adapted to determine the position of the catheter within the generated image based on the position of the catheter determined by the localization device, the imaging and interventional spatial relations and the ray geometries.

Although in above described embodiments the localization device is an EMT device, in other embodiments also other localization devices can be used like an OSS localization device.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like providing the spatial relations and determining the position of the catheter within the generated image performed by one or several units or devices can be performed by any other number of units or devices. These procedures and/or the control of the localization device, the spatial relations providing unit and the position determination unit in accordance with steps 206 to 209 of the position determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

At an imaging site an imaging device generates an image of a subject and an imaging light markers generation device generates light markers at locations on a surface of the subject before an interventional procedure is performed. At an interventional site an interventional light markers generation device generates light markers at the locations on the surface of the subject and a localization device determines the position of the catheter during the interventional procedure. A position determination unit then determines the position of a catheter within the pre-interventional image based on the position of the catheter determined by the localization device and provided spatial relations between the devices used for generating the image and the light markers and for localizing the catheter. This allows showing the position of the catheter within the pre-interventional image without necessarily using x-rays.

The invention claimed is:

1. A localization system for localizing a catheter within a subject during an interventional procedure and for being used together with an imaging system, which comprises an imaging device configured for generating an image of the subject, before the interventional procedure is performed, at an imaging site, and an imaging light markers generation device configured for generating light markers at locations on a surface of the subject, before the interventional procedure is performed, at the imaging site, the localization system comprising:
  a localization device for determining the position of the catheter during the interventional procedure at an interventional site,
  an interventional light markers generation device for generating light markers at locations on the surface of the subject, at which the imaging light markers generation device of the imaging system has also generated light markers, at the interventional site,
  a spatial relations providing unit for providing an imaging spatial relation between the imaging device of the imaging system and the imaging light markers generation device and an interventional spatial relation between the localization device and the interventional light markers generation device, and
  a position determination unit for determining the position of the catheter within the generated image based on the position of the catheter determined by the localization device and the imaging and interventional spatial relations.

2. The localization system of claim 1 wherein:
  the localization device comprises an EM field generator for determining the position of an EM position sensor arranged at a tip of the catheter based on EM signals generated by the EM field generator and the EM position sensor at the tip of the catheter;
  the interventional light markers generation device comprises light sources arranged for generating the light markers at the locations on the surface of the subject;
  the spatial relations providing unit comprises a computer programmed to provide the imaging spatial relation between the imaging device of the imaging system and the imaging light markers generation device and the interventional spatial relation between the localization device and the interventional light markers generation device; and
  the position determination unit comprises said computer programmed to determine the position of the catheter within the generated image based on the position of the catheter determined by the localization device and the imaging and interventional spatial relations.

3. A position determination system for determining a position of a catheter, which is located within a subject, in an image of the subject during an interventional procedure, the position determination system comprising:
  an imaging system, which comprises an imaging device for generating an image of the subject, before the interventional procedure is performed, at an imaging site, and an imaging light markers generation device for generating light markers at locations on a surface of the subject, before the interventional procedure is performed, at the imaging site,
  a localization system for localizing the catheter within the subject during the interventional procedure as defined in claim 1.

4. The position determination system as defined in claim 3, wherein the imaging light markers generation device comprises light sources emitting rays in accordance with a first ray geometry for generating the light markers, wherein the interventional light markers generation device comprises light sources emitting rays in accordance with a second ray geometry for generating the light markers and wherein the first ray geometry and the second ray geometry are the same.

5. The position determination system as defined in claim 3, wherein the imaging light markers generation device and the imaging device are integrated, wherein the imaging light markers generation device comprises light sources attached to the imaging device.

6. The position determination system as defined in claim 3, wherein the imaging light markers generation device and/or the interventional light markers generation device comprise a bridge structure for bridging the subject, wherein light sources for generating the light markers are attached to the bridge structure.

7. The position determination system as defined in claim 3, wherein the imaging light markers generation device and/or the interventional light markers generation device are adapted such that the different generated light markers have different visual appearances.

8. The position determination system as defined in claim 3, wherein the imaging light markers generation device and/or the interventional light markers generation device are adapted such that the different generated light markers are light points.

9. The position determination system as defined in claim 3, wherein the position determination system further comprises a subject support for supporting the subject, wherein the subject support is adapted to position the subject with six degrees of freedom.

10. The position determination system as defined in claim 3, wherein the position determination system further comprises a calibration phantom comprising first markers for marking locations at which the light markers generated by the interventional light markers generation device are to be located during a calibration procedure and second markers for marking locations at which the catheter is to be located during the calibration procedure while the localization device determines the position of the catheter, wherein the spatial relations providing unit is adapted to determine the interventional spatial relation based on the positions of the catheter, which have been determined by the localization device while the catheter was located at the second markers and the light markers were located at the first markers.

11. A position determination method for determining a position of a catheter, which is located within a subject, in an image of the subject during an interventional procedure and for being used by a position determination system, the method comprising:
  generating an image of the subject by an imaging device, before the interventional procedure is performed, at an imaging site,
  generating light markers at locations on a surface of the subject, before the interventional procedure is performed, by an imaging light markers generation device at the imaging site,
  generating light markers at the locations on the surface of the subject by an interventional light markers generation device at an interventional site, determining the position of the catheter within the subject during the interventional procedure by a localization device at the interventional site, providing an imaging spatial relation between the imaging device and the imaging light markers generation device and an interventional spatial relation between the localization device and the interventional light markers generation device by a spatial relations providing unit, and determining the position of the catheter within the generated image based on the position of the catheter determined by the localization device and the imaging and interventional spatial relations by a position determination unit.

12. The position determination method as defined in claim 11, wherein the method further includes permanently marking the locations on the surface of the subject at the imaging site and wherein the generation of the light markers at the interventional site includes generation the light markers at the marked locations on the surface.

13. The method of claim 11 further including:
generating an image of the subject, before the interventional procedure is performed with an imaging device at an imaging site;
generating light markers at locations on a surface of the subject, before the interventional procedure is performed, at the imaging site with an imaging light markers generation device; and
localizing the catheter within the subject during the interventional procedure.

14. The method of claim 13, further including:
emitting rays in accordance with a first ray geometry for generating the light markers with light sources of the imaging light markers generation device; and
emitting rays in accordance with a second ray geometry for generating the light markers with light sources of the interventional light markers generation device comprises;
wherein the first ray geometry and the second ray geometry are the same.

15. The method of claim 13, further including:
integrating the imaging light markers generation device and the imaging device;
wherein the imaging light markers generation device comprises light sources attached to the imaging device.

16. The method of claim 13, wherein
bridging a subject with the imaging light markers generation device and/or the interventional light markers generation device;
wherein light sources for generating the light markers are attached to the bridge structure.

17. The method of claim 13, wherein the different generated light markers are light points.

18. The method of claim 13, further including:
supporting the subject with a subject support;
wherein the subject support is adapted to position the subject with six degrees of freedom.

19. The method of claim 13, further including:
marking locations at which the light markers generated by the interventional light markers generation device are to be located during a calibration procedure with a calibration phantom comprising first markers; and
marking locations at which the catheter is to be located during the calibration procedure while the localization device determines the position of the catheter with second markers; and
determining the interventional spatial relation based on the positions of the catheter, which have been determined by the localization device while the catheter was located at the second markers and the light markers were located at the first markers.

20. A localization computer program for localizing a catheter within a subject during an interventional procedure, the localization computer program comprising program code in a non-transitory computer readable medium, which when executed by a computer causes:
a localization device of a localization system to determine a position of the catheter during the interventional procedure;
an imaging system, which comprises an imaging device configured for generating an image of the subject, before the interventional procedure is performed, at an imaging site, and an imaging light markers generation device configured for generating light markers at locations on a surface of the subject, before the interventional procedure is performed, at the imaging site a spatial relations providing unit of the localization system to provide an imaging spatial relation between the imaging device and the imaging light markers generation device of the imaging system and an interventional spatial relation between the localization device and the interventional light markers generation device of the localization system; and
a position determination unit of the localization system to determine the position of the catheter within an image generated by the imaging device based on the position of the catheter determined by the localization device and the imaging and interventional spatial relations.

\* \* \* \* \*